(12) United States Patent
Okihara

(10) Patent No.: US 10,130,771 B2
(45) Date of Patent: Nov. 20, 2018

(54) SYRINGE BARREL AND MOLD FOR INJECTION MOLDING

(71) Applicant: Terumo Kabushiki Kaisha, Tokyo (JP)

(72) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 168 days.

(21) Appl. No.: 15/061,667

(22) Filed: Mar. 4, 2016

(65) Prior Publication Data
US 2016/0184528 A1 Jun. 30, 2016

Related U.S. Application Data

(63) Continuation of application No. PCT/JP2014/073174, filed on Sep. 3, 2014.

(30) Foreign Application Priority Data

Sep. 6, 2013 (JP) ................... 2013-185520

(51) Int. Cl.
A61M 5/31 (2006.01)
B29C 45/37 (2006.01)
(Continued)

(52) U.S. Cl.
CPC .......... A61M 5/3129 (2013.01); A61M 5/288 (2013.01); B29C 45/261 (2013.01);
(Continued)

(58) Field of Classification Search
CPC .. A61M 5/3129; A61M 5/288; A61M 5/3134; A61M 5/31505; A61M 5/343;
(Continued)

(56) References Cited

U.S. PATENT DOCUMENTS 4,941,876 A * 7/1990 Meyer ................. A61M 5/2429 206/221
5,716,338 A * 2/1998 Hjertman ............ A61M 5/2448 604/191

(Continued)

FOREIGN PATENT DOCUMENTS

EP 2 500 052 A1 9/2012
JP 35-017448 B1 11/1960
(Continued)

OTHER PUBLICATIONS

The Extended European Search Report issued in Application No. 14842018.5 dated Feb. 22, 2017.
(Continued)

Primary Examiner — Andrew Gilbert
Assistant Examiner — Dung Ulsh
(74) Attorney, Agent, or Firm — Foley & Lardner LLP

(57) ABSTRACT

A syringe barrel includes a hollow barrel portion that has a proximal-end opening at a proximal end of the barrel portion and is configured such that a gasket is insertable from the proximal-end opening into the barrel portion. An inner peripheral portion of the barrel portion includes a tapered portion in a main area of the inner peripheral portion in an axial direction, the tapered portion having an inner diameter that gradually increases toward a distal end of the tapered portion from a proximal end of the tapered portion.

8 Claims, 10 Drawing Sheets

(51) Int. Cl.
  *B29C 45/26* (2006.01)
  *A61M 5/28* (2006.01)
  B29C 33/44 (2006.01)
  B29L 31/00 (2006.01)
  A61M 5/315 (2006.01)
  A61M 5/34 (2006.01)
  B29K 101/12 (2006.01)

(52) U.S. Cl.
  CPC ............ *B29C 45/37* (2013.01); *A61M 5/3134* (2013.01); *A61M 5/31505* (2013.01); *A61M 5/343* (2013.01); *A61M 2005/3104* (2013.01); *A61M 2005/3109* (2013.01); *A61M 2005/3131* (2013.01); *B29C 33/44* (2013.01); *B29K 2101/12* (2013.01); *B29L 2031/7544* (2013.01)

(58) Field of Classification Search
  CPC ........ A61M 2005/3104; A61M 5/3109; A61M 5/3131
  See application file for complete search history.

(56) References Cited

U.S. PATENT DOCUMENTS

| | | | | |
|---|---|---|---|---|
| 5,725,500 | A * | 3/1998 | Micheler | A61J 1/062 366/130 |
| 5,891,087 | A * | 4/1999 | Ohtani | A61M 5/284 604/190 |
| 5,935,101 | A * | 8/1999 | Kato | A61M 5/284 604/181 |
| 6,290,680 | B1 * | 9/2001 | Forsberg | A61J 1/062 141/237 |
| 8,834,449 | B2 * | 9/2014 | Machan | A61M 5/31596 604/518 |
| 2001/0008962 | A1 * | 7/2001 | Forsberg | A61J 1/062 604/232 |
| 2006/0178644 | A1 * | 8/2006 | Reynolds | A61J 1/2093 604/232 |
| 2010/0198165 | A1 * | 8/2010 | Zihlmann | A61L 2/06 604/208 |
| 2011/0182998 | A1 * | 7/2011 | Reb | A61L 24/06 424/499 |
| 2013/0200549 | A1 * | 8/2013 | Felts | A61M 5/3129 264/275 |
| 2013/0267904 | A1 * | 10/2013 | Limaye | A61M 5/3293 604/189 |
| 2014/0005636 | A1 * | 1/2014 | Wang | A61M 5/284 604/518 |
| 2014/0316342 | A1 * | 10/2014 | Kanazawa | A61M 5/284 604/191 |
| 2014/0319778 | A1 * | 10/2014 | Kawasaki | A61M 5/3129 277/440 |
| 2014/0323981 | A1 * | 10/2014 | Giraud | A61B 5/1438 604/218 |
| 2015/0224263 | A1 * | 8/2015 | Dugand | B29C 45/14622 604/218 |
| 2015/0352008 | A1 * | 12/2015 | Kucuk | A61M 5/3129 206/438 |
| 2016/0001017 | A1 * | 1/2016 | Ogawa | A61M 5/3135 604/111 |
| 2016/0008545 | A1 * | 1/2016 | Brothers | A61M 5/3134 604/506 |
| 2016/0184528 | A1 * | 6/2016 | Okihara | B29C 45/37 604/221 |
| 2016/0220758 | A1 * | 8/2016 | Ishida | A61M 5/3129 |

FOREIGN PATENT DOCUMENTS

| | | |
|---|---|---|
| JP | H7-323085 A | 12/1995 |
| JP | H07-323085 A | 12/1995 |
| WO | WO 2014/190225 A1 | 11/2014 |

OTHER PUBLICATIONS

International Search Report for PCT/JP2014/073174 dated Dec. 2, 2014.

* cited by examiner

SYRINGE BARREL AND MOLD FOR INJECTION MOLDING

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2014/073174, filed on Sep. 3, 2014, which claims priority to Japanese Patent Application No. JP2013-185520, filed on Sep. 6, 2013. The contents of these applications are hereby incorporated by reference in their entireties.

BACKGROUND

The present disclosure relates to a syringe barrel and a mold for injection molding.

Generally, a syringe barrel made of plastic is manufactured by an injection molding process (refer to JP 7-323085 A, for example). In the case of manufacturing a syringe barrel by the injection molding process, a mold for injection molding is used, and the mold includes a female mold (outer mold) formed with a cavity to form an outer surface shape of the syringe barrel and a male mold (core) to mold an inner surface shape of the syringe barrel. A molten resin is injected into a gap formed between the female mold and the male mold, and after solidification of the resin, the molded syringe barrel is removed from the mold. Thus, the syringe barrel molded in a predetermined shape can be obtained.

SUMMARY OF THE INVENTION

When removing a molded syringe barrel from a mold for injection molding, it is necessary to leave the molded syringe barrel remaining on a male mold side by relatively moving a female mold and the male mold in an axial direction, and separate (remove) the molded syringe barrel from a cavity of the female mold. However, in the case in which fitting force between the male mold and the molded syringe barrel is weaker than fitting force between the female mold and the molded syringe barrel, there may be a problem in which the molded syringe barrel cannot be removed from the cavity, and as a result, the molded syringe barrel may instead remain on the female mold side, i.e., in the cavity.

In view of the above-described problem, certain embodiments of the present invention are directed to providing a syringe barrel and a mold for injection molding capable of preventing a molded syringe barrel from remaining in a cavity of the female mold at the time of removing the molded syringe barrel from the inside of the mold when manufacturing the syringe barrel by injection molding.

To achieve the above object, certain embodiments of the present invention provide a syringe barrel comprising a hollow barrel portion that has a proximal-end opening at a proximal end of the barrel portion and is configured that a gasket is inserted from the proximal-end opening into the barrel portion. An inner peripheral portion of the barrel portion includes a tapered portion in a main area of the inner peripheral portion in an axial direction and the tapered portion has an inner diameter gradually increased toward a distal end of the tapered portion from a proximal end of the tapered portion.

In this syringe barrel, the inner peripheral portion of the barrel portion includes the tapered portion (reversed taper) having the inner diameter gradually increased toward the distal end. Therefore, the molded syringe barrel is prevented from remaining in the cavity of the female mold at the time of mold separation in injection molding. More specifically, the molded syringe barrel is fitted to the core with appropriate force by a function of the reversed taper at the time of mold separation by moving the female mold relative to the male mold adapted to mold the inner peripheral surface of the syringe barrel. Therefore, the molded syringe barrel can be surely separated from the cavity of the female mold and made to remain on the male mold side. Further, the syringe manufactured by using the syringe barrel provided with such a reversed taper provides excellent operability because sliding resistance is reduced when the gasket is moved forward at the time of use.

In the above-described syringe barrel, 50% or more of a length of the barrel portion may be the tapered portion in the inner peripheral portion of the barrel portion. With this structure, the molded syringe barrel can be effectively prevented from remaining in the cavity of the outer mold at the time of mold separation in injection molding.

In the above-described syringe barrel, substantially an entire area in the axial direction of the inner peripheral portion of the barrel portion may be the tapered portion. With this structure, the molded syringe barrel can be surely prevented from remaining in the cavity of the female mold at the time of mold separation in injection molding.

In the above-described syringe barrel, a difference between an inner diameter at the proximal end of the tapered portion and an inner diameter at the distal end of the tapered portion may be 0.01 to 0.07 mm. With this structure, the molded syringe barrel can be effectively prevented from remaining in the cavity of the female mold at the time of injection molding without having any trouble in separating the molded syringe barrel from the male mold.

In the above-described syringe barrel, an axial length of the barrel portion may be 50 to 60 mm, and the difference between the inner diameter at the proximal end of the tapered portion and the inner diameter at the distal end of the tapered portion may be 0.02 to 0.05 mm. With this structure, it is possible to obtain a syringe capable of preventing the molded syringe barrel from remaining in the cavity in injection molding and having volume of about 1 mL.

In the above-described syringe barrel, a curved portion may be provided on a distal end side of the tapered portion at the inner peripheral portion of the barrel portion, interposing a distal-end side straight portion having a constant inner diameter. With this structure, even in the case of providing the curved portion (portion R) on the distal end side of the tapered portion, dimensional accuracy is easily achieved due to presence of the distal-end side straight portion.

In the above-described syringe barrel, a curved portion may be provided on a proximal end side of the tapered portion at the inner peripheral portion of the barrel portion, interposing a proximal-end side straight portion having a constant inner diameter. With this structure, even in the case of providing the curved portion (portion R) on the proximal end side of the tapered portion, dimensional accuracy is easily achieved due to presence of the proximal-end side straight portion.

In the above-described syringe barrel, the syringe barrel is formed of a cyclic olefin polymer or a cyclic olefin copolymer. Since these resins belong to a hard type as the resin, when an undercut is locally provided at the barrel portion, there may be possibility that the barrel portion is cracked at the time of mold separation. However, according to the present invention, occurrence of such a crack at the time of mold separation can be prevented because the reversed taper is provided in a wide range.

Further, the present invention provides a mold for injection molding adapted to mold a syringe barrel by injection molding. The syringe barrel comprises a hollow barrel portion that has a proximal-end opening at a proximal end and is configured that a gasket is inserted from the proximal-end opening into the barrel portion. The mold for injection molding includes: a female mold having a recessed portion to mold an outer surface of the syringe barrel; and a male mold having a core provided with a barrel portion molding section to mold an inner peripheral surface of the barrel portion. The barrel portion molding section of the core includes: an opening molding section to mold the proximal-end opening at the proximal end; and a tapered molding section in a main area of the barrel portion molding section in an axial direction, which the tapered molding section has an outer diameter gradually increased toward a distal end of the tapered molding section from a proximal end of the tapered molding section.

According to the syringe barrel and the mold for injection molding in the present invention, the molded syringe barrel can be prevented from remaining in the cavity of the female mold at the time of removing the syringe barrel that is the molded syringe barrel from the inside of the mold in manufacturing the syringe barrel by injection molding.

DETAILED DESCRIPTION

In the following, some preferred embodiments of a syringe barrel and a mold for injection molding according to the present invention will be described with reference to the attached drawings.

First Embodiment

Figure 1:
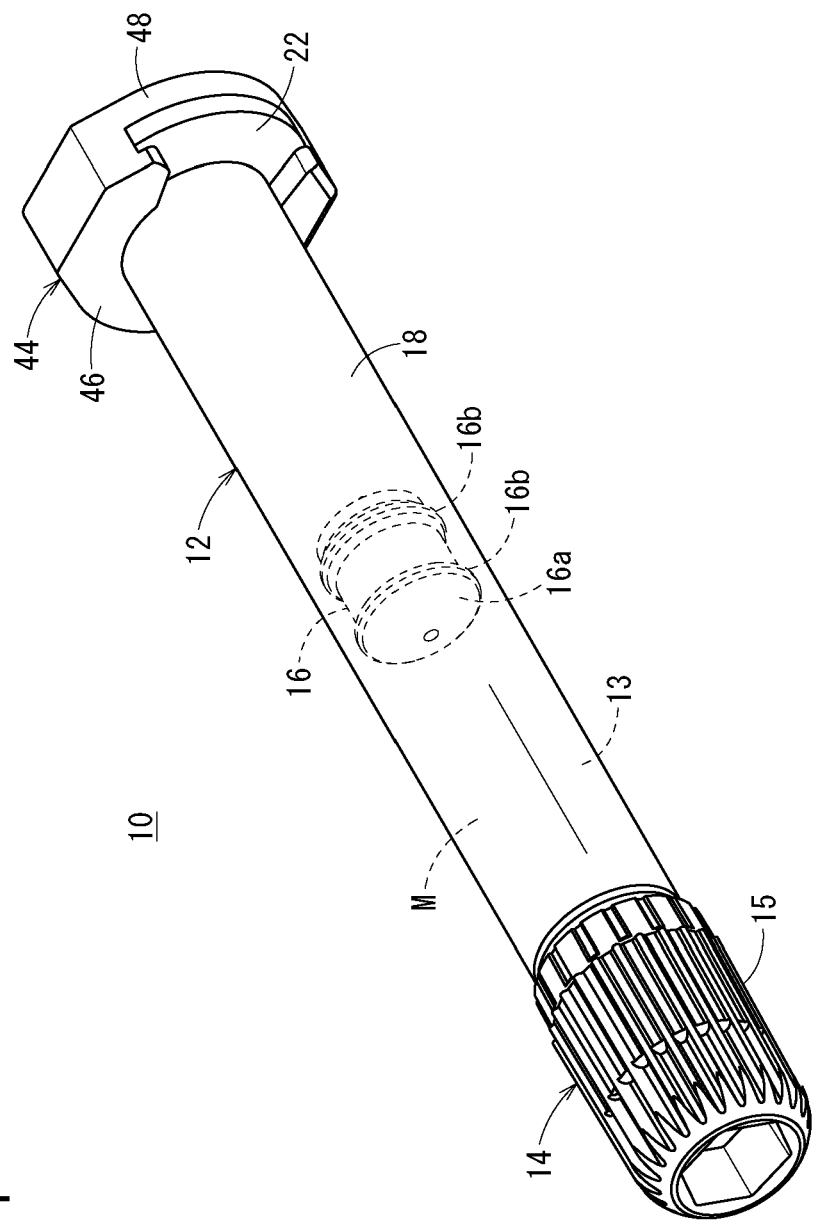
FIG. 1 is a perspective view illustrating a syringe including a syringe barrel according to a first embodiment of the present invention.

FIG. 1 is a perspective view illustrating a syringe 10 including a syringe barrel 12 according to a first embodiment of the present invention.

The syringe 10 includes, as main components, the syringe barrel 12, a cap 14 to seal a distal end opening of the syringe barrel 12, a gasket 16 capable of liquid-tightly sliding inside the syringe barrel 12, and a drug M filled in a filling chamber 13 formed inside the syringe barrel 12. The syringe 10 is formed as a prefilled syringe preliminarily filled with the drug M.

When the syringe 10 is used, the syringe 10 is connected with a separate prefilled syringe having a male lure and filled with medical liquid (liquid for dilution or dissolution). Further, in the connected state, intended medicinal solution is prepared by suctioning the drug inside the syringe 10 into the separate prefilled syringe filled with the medical liquid and mixing the drug M with the medical liquid inside the separate prefilled syringe.

Figure 2:
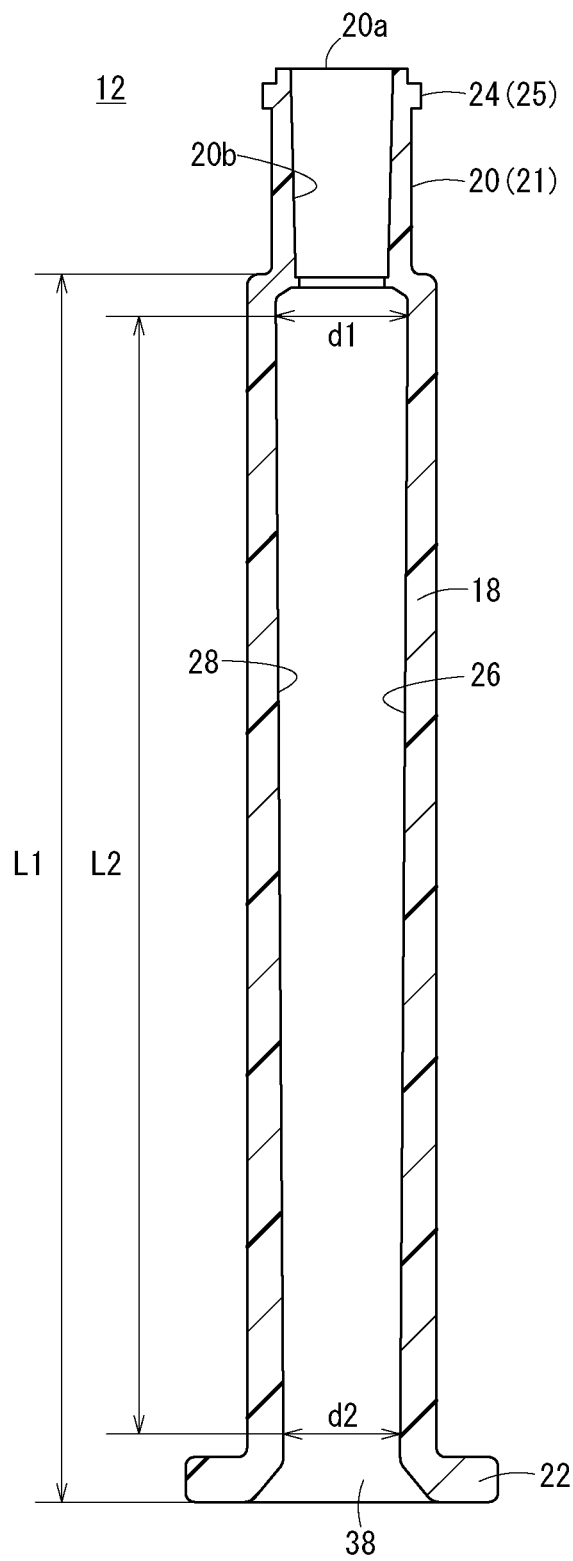
FIG. 2 is a longitudinal sectional view illustrating the syringe barrel illustrated in FIG. 1.

As illustrated in FIG. 2, the syringe barrel 12 includes a hollow barrel portion 18 constituting a main portion thereof, a hollow cylinder tip portion 20 provided at a distal end of the barrel portion 18, and a flange 22 formed in a manner projecting radially outward from a proximal end of the barrel portion 18.

The barrel portion 18 is a hollow cylindrical shaped portion into which the gasket 16 is inserted in a manner slidable at an inner peripheral portion 26 thereof. An axial length L1 of the barrel portion 18 is set to, for example, 45 to 160 mm although the length may be varied by volume of the syringe 10. In the case in which the syringe barrel 12 is formed to have volume of 1 mL, the axial length L1 of the barrel portion 18 is set to, for example, 50 to 60 mm.

The inner peripheral portion 26 of the barrel portion 18 includes, in a main area in an axial direction, a tapered portion 28 having an inner diameter that gradually increases toward the distal end from the proximal end. An axial length L2 of the tapered portion 28 is set to, for example, 50% or more of the axial length L1 of the barrel portion 18. Otherwise, the tapered portion 28 may be provided in substantially an entire area in an axial direction of the inner peripheral portion 26 of the barrel portion 18. In this case, the length L2 of the tapered portion 28 is set to 70% or more of the length L1 of the barrel portion 18, more preferably, 80% or more thereof.

Since the inner diameter of the tapered portion 28 is thus gradually increased toward the distal end from the proximal end, an inner diameter of the tapered portion 28 becomes largest at the distal end and smallest at the proximal end. In other words, an inner diameter d1 at the distal end of the tapered portion 28 is larger than an inner diameter d2 at the proximal end.

In FIG. 2, a gradient of the tapered portion 28 is illustrated in an exaggerative manner for easy understanding for presence of the tapered portion 28, but preferably the gradient of the tapered portion 28 is slight relative to an axial line of the syringe barrel 12. In other words, a difference between the inner diameter d2 at the proximal end and the inner diameter d1 at the distal end (d2−d1) is very small. Therefore, the difference between the inner diameter d2 at the proximal end and the inner diameter d1 at the distal end of the tapered portion 28 is set to, for example, 0.01 to 0.07 mm. In the case in which the syringe barrel 12 is formed to have volume of 1 mL, the difference between the inner diameter d2 at the proximal end and the inner diameter d1 at the distal end of the tapered portion 28 is set to, for example, 0.02 to 0.05 mm.

Note that an outer diameter of the barrel portion 18 (not including the flange 22 portion) is axially constant, or gradually reduced toward the distal end from the proximal end.

Figure 3A:
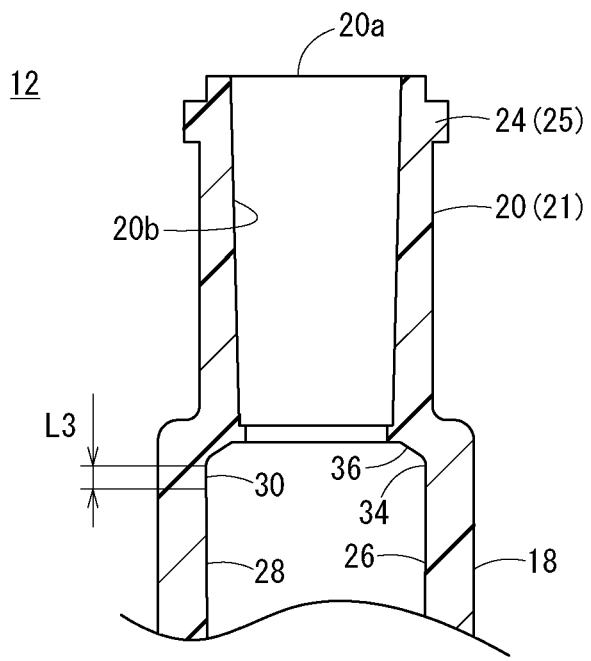
FIG. 3A is an enlarged view illustrating a distal end side of the syringe barrel illustrated in FIG. 2.

As illustrated in FIG. 3A, in the inner peripheral portion 26 of the barrel portion 18, a distal-end side straight portion 30 having an axially constant inner diameter is provided continuous to the distal end side of the tapered portion 28. The inner diameter of the distal-end side straight portion 30 is same as the inner diameter d1 at the distal end of the tapered portion 28 (refer to FIG. 2). An axial length L3 of the distal-end side straight portion 30 may be short and is set to, for example, 0.1 to 5 mm.

Further, a distal-end side tapered portion 36 having an inner diameter gradually reduced in the distal end direction is provided on the distal end side of the distal-end side straight portion 30, with a curved portion 34 (portion R) interposed between the distal-end side tapered portion 36 and the distal-end side straight portion. Since the distal-end side straight portion 30 is thus interposed between the tapered portion 28 and the curved portion 34, dimensional accuracy is easily achieved by injection molding for the diameter at the distal end of the tapered portion 28.

Figure 3B:
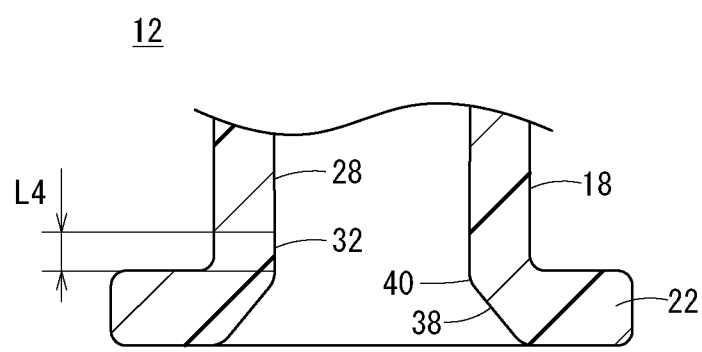
FIG. 3B is an enlarged view illustrating a proximal end side of the syringe barrel illustrated in FIG. 2.

As illustrated in FIG. 3B, in the inner peripheral portion 26 of the barrel portion 18, a proximal-end side straight portion 32 having an axially constant inner diameter is provided continuous to the proximal end side of the tapered portion 28. The inner diameter of the proximal-end side straight portion 32 is same as the inner diameter d2 at the proximal end of the tapered portion 28 (refer to FIG. 2). An axial length L4 of the proximal-end side straight portion 32 may be short and is set to, for example, 0.1 to 5 mm.

Further, on the proximal end side of the proximal-end side straight portion 32, a proximal-end opening 38 is provided as a proximal-end side tapered portion having an inner diameter reduced in the distal end direction, with a curved portion 40 (portion R) interposed between the proximal-end straight portion 32 and the proximal-end opening 38. Since the proximal-end side straight portion 32 is thus interposed between the tapered portion 28 and the curved portion 40, dimensional accuracy is easily achieved by injection molding for the diameter at the proximal end of the tapered portion 28.

In FIG. 2, the cylinder tip portion 20 projects in the distal end direction from the distal end portion of the syringe barrel 12 while having the reduced diameter relative to the syringe barrel 12. The cylinder tip portion 20 includes a tapered inner surface 20b in which a female lure 21 into which the male lure can be inserted and connected, and an inner diameter is increased in the distal end direction.

A fixing portion 24 adapted to detachably fix the cap 14 illustrated in FIG. 1 is provided at a distal-end outer peripheral portion of the cylinder tip portion 20. According to the present embodiment, the fixing portion 24 is a screw portion (male screw) that can be screwed with the cap 14. More specifically, in the present example illustrated, the fixing portion 24 is formed of two engagement projections 25 projecting in directions opposing to each other based on the axial line of the syringe barrel 12.

The volume of the syringe barrel 12 is not limited to specific volume and can be set in a range of, for example, 0.5 to 100 mL. Further, in this case, the volume of the syringe barrel 12 may be set to respective volume of, for example, 0.5 mL, 1 mL, 5 mL, 10 mL, 20 mL, 30 mL, 50 mL, and 100 mL.

Materials constituting the syringe barrel 12 may be various kinds of resins such as polypropylene, polyethylene, polystyrene, polyamide, polycarbonate, polyvinyl chloride, poly-(4-methyl pentene-1), an acrylic resin, an acrylonitrile-butadiene-styrene copolymer, polyester like polyethylene terephthalate, a cyclic olefin polymer, and a cyclic olefin copolymer. Among them, the resins such as the polypropylene, cyclic olefin polymer, and cyclic olefin copolymer are preferable because these resins are easily molded and have heat resistance.

The cap 14 illustrated in FIG. 1 includes a sealing member (not illustrated) formed of an elastic member that seals a distal end opening 20a of the cylinder tip portion 20 (refer to FIG. 2), and a cylindrical main body 15 that supports the seal member. An inner peripheral portion of the main body 15 is provided with a female screw (not illustrated) to be screwed with the fixing portion 24 (engagement projection 25) provided at the cylinder tip portion 20. In a pre-use state in which the cap 14 is attached to the cylinder tip portion 20, the distal end opening 20a is liquid-tightly sealed by the cap 14 and the drug M is prevented from leaking out from the distal end opening 20a.

Note that an engagement structure (fixing structure) between the cap 14 and the cylinder tip portion 20 is not limited to the above-described screw fitting. For example, there may be a structure in which an engagement projection is provided at an outer peripheral surface of the cylinder tip portion 20 and further an engagement projection is provided at an inner peripheral surface of the main body 15 of the cap 14, and these engagement projections are hooked each other. In this case, when the cap 14 is pulled in the distal end direction, the main body is elastically deformed, and the engagement projection on the main body 15 side moves over the engagement projection on the cylinder tip portion 20 side, thereby achieving removal of the cap 14 from the cylinder tip portion 20.

The gasket 16 is inserted into the syringe barrel 12. A distal end surface 16a of the gasket 16 has a tapered shape that is tapered toward the distal end. A plurality of ring-shaped sealing projections 16b is formed at intervals in the axial direction at an outer peripheral portion of the gasket 16 (two sealing projections are formed in the drawing). The sealing projections 16b closely contacts the inner peripheral surface of the syringe barrel 12 (barrel portion 18) in a state that the gasket 16 is inserted into the syringe barrel 12. This enables the gasket 16 to liquid-tightly slide inside the syringe barrel 12.

Figure 5:
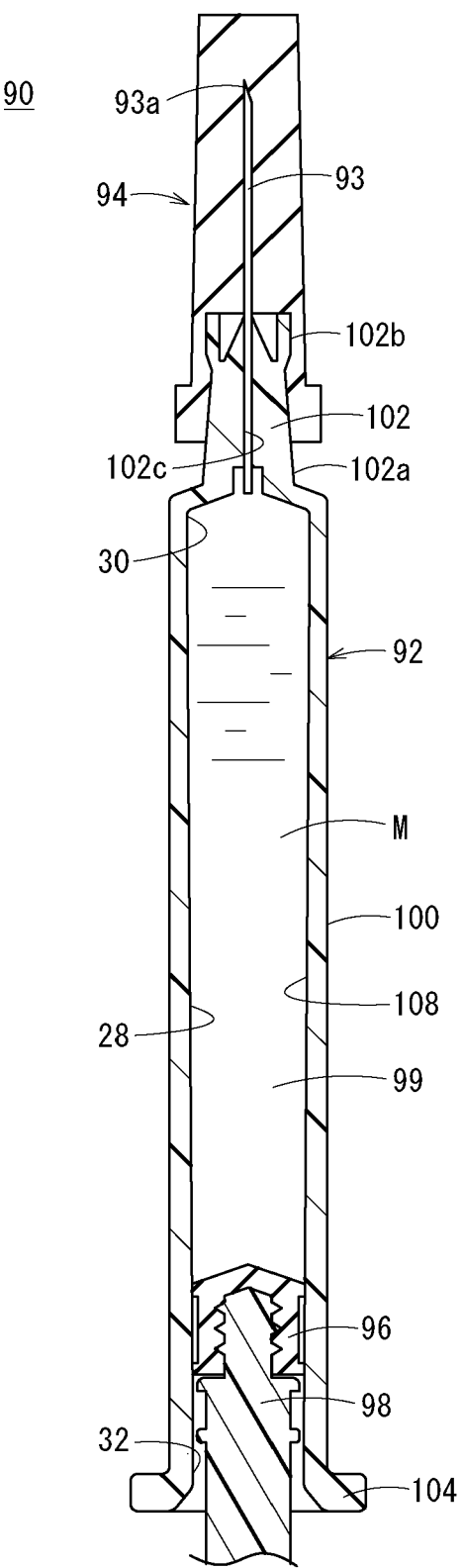
FIG. 5 is a longitudinal sectional view illustrating a syringe including a syringe barrel according to a second embodiment of the present invention.

The gasket 16 is provided with a fitting recessed portion opened to the proximal end side and formed with a female screw at an inner peripheral portion (refer to gasket 96 in FIG. 5). If necessary, the fitting recessed portion can be screwed with a distal end portion of a pusher not illustrated.

Materials constituting the gasket 16 may be, for example, various kinds of rubber materials such as natural rubber, butyl rubber, isoprene rubber, butadiene rubber, styrene-butadiene rubber, and silicone rubber, various kinds of thermoplastic elastomer such as polyurethane-based, polyester-based, polyamide-based, olefin-based and styrene-based thermoplastic elastomer, mixtures thereof, and so on.

The drug M may be any of a powder drug, a freeze-dried drug, a solid drug, a liquid drug, and so on. As examples of such drugs, for example, following drugs can be listed: protein preparation, an antitumor drug, vitamin preparation (multivitamin preparation), various kinds of amino acids, antithrombotic agents such as heparin, insulin, antibiotics, antitumor agents, painkiller, cardiotonic agents, intravenous anesthetics, medical drugs, antiperkinson agents, anti-ulcer agents, adrenal cortex hormones, corticosteroid, antiarrhythmic agents, and so on.

Meanwhile, in the syringe 10, a gasket stopper 44 is detachably attached to the proximal end portion (flange 22) of the syringe barrel 12 in order to prevent the gasket 16 from coming off from the syringe barrel 12 in the proximal end direction. The gasket stopper 44 includes a stopper plate 48 contacting a proximal end surface of the flange 22, and a semicircle engagement plate 46 in which a side to be engaged with the flange 22 of the syringe barrel 12 opened. The barrel portion 18 of the syringe barrel 12 is inserted into the inside of the engagement plate 46, and further the gasket stopper 44 is attached to the proximal end portion of the syringe barrel 12 by inserting the flange 22 between the stopper plate 48 and the engagement plate 46.

Next, a mold for injection molding 50 in order to mold the above-described syringe barrel 12 by injection molding will be described with reference to FIG. 4.

The mold for injection molding 50 includes a female mold 52 (outer mold) having a cavity 53 that is a recessed portion to mold an outer surface shape of the syringe barrel 12, and a male mold 54 to mold an inner surface shape of the syringe barrel 12. In a state that a later-described core 65 of the male mold 54 is disposed inside the female mold 52, a gap 55 corresponding to a shape of the syringe barrel 12 to be molded is formed between the female mold 52 and the male mold 54.

The female mold 52 includes: a first mold 56 formed with molding sections 56a, 56b to mold respective outer surface shapes of the barrel portion 18 and the flange 22 of the syringe barrel 12: second and third molds 60, 62 respectively formed with molding sections 61, 63 to mold an outer surface shape of the cylinder tip portion 20; and a fourth mold 80 formed with a female lure molding section 82 to mold an inner surface of the cylinder tip portion 20. In the female mold 52, the cavity 53 is formed of the molding sections 56a, 56b, 61, 63 and the female lure molding section 82.

The first mold 56 is provided with an injection passage 57 in order to inject a molten resin into the gap 55. The injection passage 57 is in communication with the gap 55. The female lure molding section 82 of the fourth mold 80 has a gradient equal to a gradient of the inner surface 20b of the cylinder tip portion 20.

In the syringe barrel 12 according to the present embodiment, the fixing portion 24 projecting outward is provided at the cylinder tip portion 20. Therefore, a mold cannot be separated by relatively moving the cylinder tip portion 20 and the mold adapted to mold the outer surface shape of the cylinder tip portion 20 in the axial direction at the time of mold separation in injection molding. Therefore, the mold to mold the outer surface shape of the cylinder tip portion 20 is divided into the second mold 60 and the third mold 62 in order to enable mold separation after molding.

The molding section 61 of the second mold 60 is a unit to mold a half of the outer surface shape (circumferentially half) of the cylinder tip portion 20, and is a groove portion having a cross-section formed in a substantially circular arc. The molding section 63 of the third mold 62 is a unit to mold the other half of the outer surface shape of the cylinder tip portion 20, and is a groove portion having a cross-section formed in a substantially circular arc. An entire length and entire circumference of the outer surface shape of the cylinder tip portion 20 are molded by the second mold 60 and the third mold 62.

The male mold 54 includes: the core 65 to mold the inner surface (inner peripheral portion 26) of the barrel portion 18 and the proximal-end opening 38; and a holding mold 58 provided with an insertion through-hole 58a through which the core 65 is inserted. More specifically, the core 65 includes a barrel portion molding section 66 to form the inner surface of the barrel portion 18 and an opening molding section 68 to mold the proximal-end opening 38. Further, the holding mold 58 includes a molding section 59 to mold a proximal end surface of the flange 22.

The barrel portion molding section 66 includes, in the main area in the axial direction, a tapered molding section 67 having an outer diameter gradually increased toward the distal end from the proximal end. The tapered molding section 67 is a unit to mold the tapered portion 28 in the syringe barrel 12 and is provided in a range indicated by an arrow A in FIG. 4. The tapered molding section 67 has a gradient equal to the gradient of the tapered portion 28 (inclination relative to the axial line of the syringe barrel 12).

Figure 4:
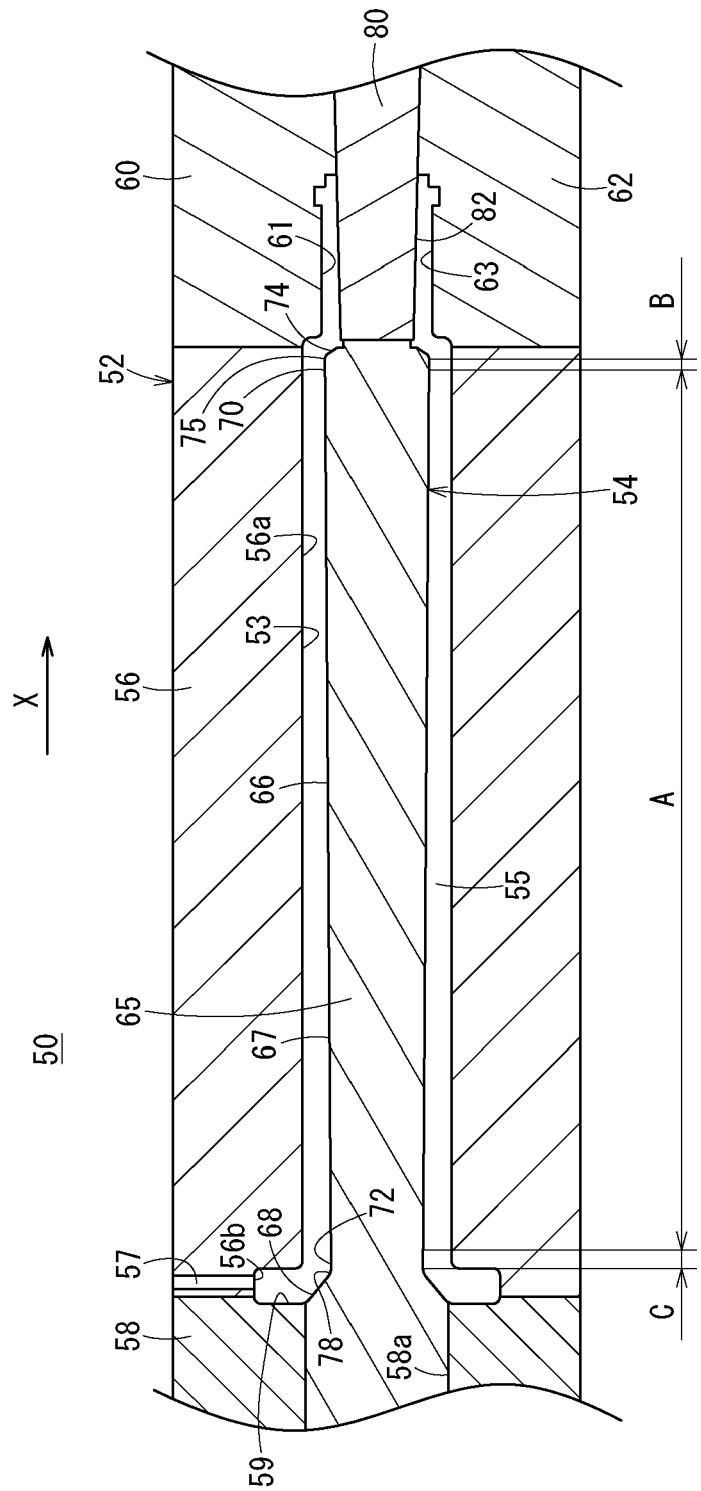
FIG. 4 is a longitudinal sectional view illustrating a mold for injection molding in order to mold the syringe barrel illustrated in FIG. 1.

As illustrated in FIG. 4, in the barrel portion molding section 66, the a distal-end side straight molding section 70 having an outer diameter constant in the axial direction is provided continuous to the distal end side of the tapered molding section 67. The distal-end side straight molding section 70 is a unit to mold the distal-end side straight portion 30 in the syringe barrel 12, and is provided in a range indicated by an arrow B in FIG. 4. The distal-end side straight molding section 70 has an inner diameter equal to the outer diameter at the distal end of the tapered molding section 67.

Further, a distal-end side tapered molding section 74 having an outer diameter reduced in the distal end direction is provided on the distal end side of the distal-end side straight molding section 70, with a curved molding section 75 (R molding section) interposed between the distal-end side tapered molding section 74 and the distal-end side straight molding section 70. The curved molding section 75 is a unit to mold the curved portion 34 in the syringe barrel 12 (refer to FIG. 3A). The distal-end side tapered molding section 74 is a unit to mold the distal-end side tapered portion 36 in the syringe barrel 12.

As illustrated in FIG. 4, in the barrel portion molding section 66, a proximal-end side straight molding section 72 having an outer diameter constant in the axial direction is provided continuous to the proximal end side of the tapered molding section 67. The proximal-end side straight molding section 72 is a unit to mold the proximal-end side straight portion 32 in the syringe barrel 12, and is provided in a range indicated by an arrow C in FIG. 4. The proximal-end side straight molding section 72 has an outer diameter equal to the outer diameter at the proximal end of the tapered molding section 67.

Further, the opening molding section 68 is provided on the proximal end side of the proximal-end side straight molding section 72 as a proximal-end side tapered molding section having an outer diameter reduced in the distal end direction, with a curved molding section 78 (R molding section) interposed between the opening molding section 68 and the proximal-end straight molding section 72. The curved molding section 78 is a unit to mold the curved portion 40 in the syringe barrel 12 (refer to FIG. 3B).

The syringe barrel 12 and the mold for injection molding 50 according to the present embodiment basically have the above-described structure, and functions and effects thereof will be described below.

First, the mold for injection molding 50 is set in a state illustrated in FIG. 4 in order to mold the syringe barrel 12 by using the above-described mold for injection molding 50. More specifically, the core 65 of the male mold 54 is inserted into the female mold 52, and the gap 55 having a shape corresponding to the syringe barrel 12 is formed between the female mold 52 and the male mold 54. Next, the molten resin is injected into the gap 55 via the injection passage 57. Then, after the resin is solidified, the molded syringe barrel 12 is removed from the mold for injection molding 50 (removal process).

In the removal process, first the fourth mold 80 is pulled out from the cylinder tip portion 20 by moving the fourth mold 80 in an X-direction in FIG. 4. Almost at the same time, the second mold 60 and the third mold 62 are moved in a direction separating from each other (vertical direction in FIG. 4), thereby separating the second mold 60 and the third mold 62 from the cylinder tip portion 20.

Next, the first mold 56 is separated from the syringe barrel 12 by axially moving the first mold 56 relative to the male mold 54. More specifically, the first mold 56 is separated from the syringe barrel 12 by moving the first mold 56 in the X-direction while keeping the position of the male mold 54. In this case, the tapered molding section 67 having the outer diameter that gradually increases toward the distal end is provided at the core 65, and the tapered portion 28 having the inner diameter that gradually increases toward the distal end is formed at the inner peripheral portion 26 of the barrel portion 18 of the syringe barrel 12 (refer to FIG. 2). Therefore, fitting force between the core 65 and the barrel portion 18 is stronger than fitting force between the first mold 56 and the barrel portion 18. Therefore, along with movement of the first mold 56 in the X-direction, the syringe barrel 12 is surely separated (removed) from the first mold 56 while being held at the core 65.

Next, the syringe barrel 12 is separated from the core 65 by axially moving the holding mold 58 relative to the core 65. More specifically, when the holding mold 58 is moved in the X-direction while keeping the position of the core 65, the syringe barrel 12 is pushed in the distal end direction and moved relative to the core 65. This separates the syringe barrel 12 from the core 65. Meanwhile, the barrel portion 18 of the syringe barrel 12 may be grasped by a chuck or the like and pulled out from the core 65 without moving the holding mold 58 relative to the core 65.

In this case, the gradients of the tapered portion 28 formed in the syringe barrel 12 and the tapered molding section 67 formed at the core 65 are slight. Therefore, there is no problem in moving the syringe barrel 12 relative to the core 65 in the distal end direction. More specifically, along with movement of the syringe barrel 12 relative to the core 65 in the distal end direction, the diameter of the barrel portion 18 is increased (deformed) within an elastic limit. Therefore, the syringe barrel 12 can be separated from the core 65 without damage.

In the above-described manner, the syringe barrel 12 is removed from the mold for injection molding 50.

As described above, according to the syringe barrel 12 of the present embodiment, the tapered portion 28 having the inner diameter that gradually increases toward the distal end (gentle reverse taper) is provided at the inner peripheral portion 26 of the barrel portion 18. Therefore, the molded syringe barrel is prevented from remaining in the cavity 53 of the female mold 52 at the time of mold separation in injection molding. More specifically, when the mold is separated by moving the male mold 54 (core 65) relative to the female mold 52 (first mold 56) to mold the outer peripheral surface of the syringe barrel 12, the molded syringe barrel is fitted to the core 65 with appropriate holding force by the function of the gently reversed taper. Therefore, the molded syringe barrel can be surely separated from the cavity 53 of the first mold 56 and made to remain on the core 65 side. Further, the syringe 10 manufactured by using the syringe barrel 12 provided with the gently reversed taper provides excellent operability because sliding resistance is reduced when the gasket 16 is moved forward at the time of use.

In this case, when 50% or more of the length L1 of the barrel portion 18 is the tapered portion 28 at the inner peripheral portion 26 of the barrel portion 18, the syringe barrel 12 can be effectively prevented from remaining in the cavity 53 of the female mold 52 at the time of mold separation in injection molding. Further, when the substantially entire area in the axial direction of the inner peripheral portion 26 of the barrel portion 18 is the tapered portion 28, the syringe barrel 12 can be surely prevented from remaining in the cavity 53 of the female mold 52 at the time of mold separation in injection molding.

In the case in which the difference between the inner diameter d2 at the proximal end and the inner diameter d1 at the distal end (d2−d1) is 0.01 to 0.07 mm in the tapered portion 28, the syringe barrel 12 can be effectively prevented from remaining in the cavity 53 of the female mold 52 (first mold 56) at the time of mold separation in injection molding without any problem in separating the syringe barrel 12 from the male mold 54 (core 65).

Particularly, when the axial length of the barrel portion 18 is 50 to 60 mm and the difference between the inner diameter d2 at the proximal end and the inner diameter d1 at the distal end of the tapered portion 28 is 0.02 to 0.05 mm, it is possible to obtain the syringe 10 that can effectively prevent the molded syringe barrel from remaining in the cavity and has the volume of about 1 mL.

The present invention is especially useful in the case in which the syringe barrel 12 is formed of a cyclic olefin polymer or a cyclic olefin copolymer. Since these resins belong to a hard type as the resin, when an undercut is locally provided at the barrel portion 18, there may possibility that the undercut may become high in order to surely prevent the molded syringe barrel from remaining in the cavity and the barrel portion 18 is cracked at the time of mold separation. However, according to the present embodiment, occurrence of such a crack can be effectively prevented at the time of mold separation because the reversed taper (tapered portion 28) is provided in the main area of the inner peripheral portion 26 of the barrel portion 18 in an axial direction. Note that the undercut may also be locally provided at the barrel portion 18 in the present embodiment.

In the case of the present embodiment, the curved portion 34 is provided on the distal end side of the tapered portion 28 at the inner peripheral portion 26 of the barrel portion 18, with the distal-end side straight portion 30 having the constant inner diameter interposing the curved portion 34 and the tapered portion 28. With this structure, even in the case of providing the curved portion 34 (portion R) on the distal end side of the tapered portion 28, dimensional accuracy for the diameter at the distal end of the tapered portion 28 is easily achieved due to presence of the distal-end side straight portion 30.

In the case of the present embodiment, the curved portion 40 is provided on the proximal end side of the tapered portion 28 at the inner peripheral portion 26 of the barrel portion 18, with the proximal-end side straight portion 32 having the constant inner diameter interposing the curved portion 40 and the tapered portion 28. With this structure, even in the case of providing the curved portion 40 (portion R) on the proximal end side of the tapered portion 28, dimensional accuracy is easily achieved for the diameter at the proximal end of the tapered portion 28 due to presence of the proximal-end side straight portion 32.

Second Embodiment

FIG. 5 is a longitudinal sectional view illustrating a syringe 90 including a syringe barrel 92 according to a second embodiment of the present invention. In the following, portions different from a first embodiment in the syringe barrel 92 will be mainly described.

The syringe 90 includes, as main components, the syringe barrel 92, a needle 93 fixed at a distal end of the syringe barrel 92, a cap 94 to seal a distal end opening of the needle 93, a gasket 96 capable of liquid-tightly sliding inside the syringe barrel 92, a pusher 98 having a distal end connected to the gasket 96, and a drug M filled in a filling chamber 99 formed inside the syringe barrel 92. Thus, the syringe 90 is formed as a prefilled syringe preliminarily filled with the drug M.

The syringe barrel 92 includes a hollow barrel portion 100 constituting a main portion thereof, a cylinder tip portion 102 provided at a distal end of the barrel portion 100, and a flange 104 formed in a manner projecting radially outward from a proximal end of the barrel portion 100.

The barrel portion 100 is a hollow cylindrical shaped portion into which the gasket 96 is inserted in a manner slidable at an inner peripheral portion thereof. Same as an inner peripheral portion 26 of a barrel portion 18 according to the first embodiment, an inner peripheral portion 108 of the barrel portion 100 includes a tapered portion 28, a distal-end side straight portion 30, and a proximal-end side straight portion 32.

Figure 6A:
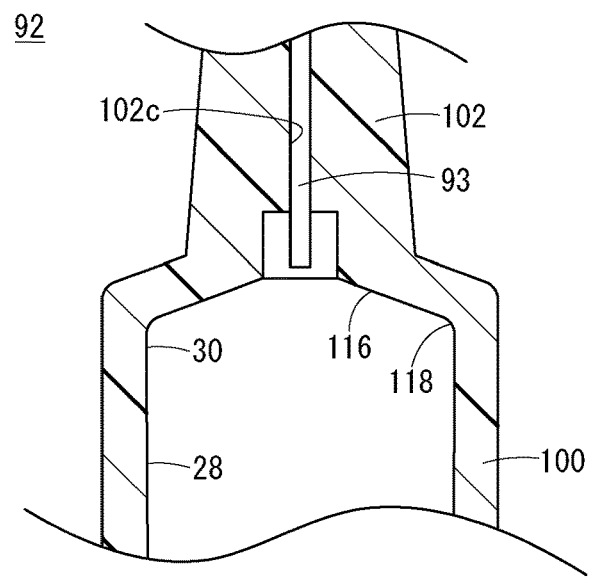
FIG. 6A is an enlarged view illustrating a distal end side of the syringe barrel illustrated in FIG. 5.

As illustrated in FIG. 6A, a distal-end side tapered portion 116 having an inner diameter gradually reduced in the distal end direction is provided on a distal end side of the distal-end side straight portion 30, with a curved portion 118 (portion R) interposed between the distal-end side tapered portion 116 and the distal-end side straight portion 30. Since the distal-end side straight portion 30 is thus interposed between the tapered portion 28 and the curved portion 118, dimensional accuracy is easily achieved by injection molding for the diameter at the distal end of the tapered portion 28.

Figure 6B:
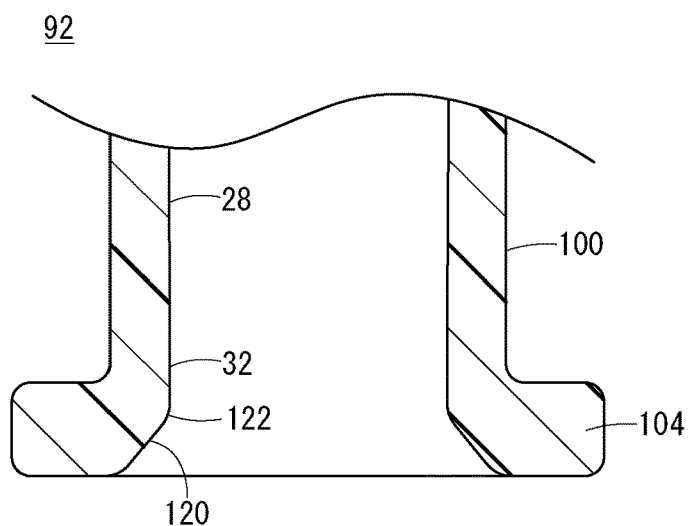
FIG. 6B is an enlarged view illustrating a proximal end side of the syringe barrel illustrated in FIG. 5.

As illustrated in FIG. 6B, on the proximal end side of the proximal-end side straight portion 32, a proximal-end opening 120 is provided as a proximal-end side tapered portion having an inner diameter reduced in the distal end direction, with a curved portion 122 (portion R) interposed between the proximal-end side straight portion 32 and the proximal-end opening 120. Since the proximal-end side straight portion 32 is thus interposed between the tapered portion 28 and the curved portion 122, dimensional accuracy is easily achieved by injection molding for the diameter at the proximal end of the tapered portion 28.

In FIG. 5, the cylinder tip portion 102 having a reduced diameter relative to the barrel portion 100 projects in the distal end direction from the distal end portion of the barrel portion 100. The cylinder tip portion 102 includes a needle holding portion 102a to hold the needle 93, and an enlarged diameter portion 102b having a diameter enlarged on the distal end side of the needle holding portion 102a. The needle holding portion 102a is formed with a needle holding hole 102c that axially passes therethrough, and a proximal end side of the needle 93 is inserted through and held by the needle holding hole 102c.

Volume of the syringe barrel 92 is not limited to specific volume, and the volume can be set in a range of, for example, 0.5 to 100 mL. Further, in this case, the volume of syringe barrel 92 may be set to respective volume of, for example, 0.5 mL, 1 mL, 5 mL, 10 mL, 20 mL, 30 mL, 50 mL, and 100 mL.

Materials constituting the syringe barrel 92 may be those exemplified as materials constituting the syringe barrel 12 according to the first embodiment.

The cap 94 has a bottomed cylindrical shape having a proximal end side opened, and is formed of an elastic material. A needle tip 93a of the needle 93 is stuck to a distal end portion of the cap 94 in a state that the cap 94 is attached to the cylinder tip portion 102. This seals the distal end opening of the needle 93, and the drug M is prevented from leaking out from the distal end opening of the needle 93 in a pre-use state in which the cap 94 is attached to the cylinder tip portion 102.

The gasket 96 has a structure same as a gasket 16 of the syringe 10 illustrated in FIG. 1. In FIG. 5, the pusher 98 is connected to the gasket 96, but the pusher 98 may also be separated from the gasket 96 before use and the pusher 98 may be connected to the gasket 96 at the time of use.

Next, a mold for injection molding 126 in order to mold the above-described syringe barrel 92 by injection molding will be described with reference to FIG. 7.

The mold for injection molding 126 includes: a female mold 128 (outer mold) having a cavity 129 that is a recessed portion to mold an outer surface of the syringe barrel 92; and a male mold 130 to form an inner surface of the syringe barrel 92. In a state that a later-described core 142 of the male mold 130 is disposed inside the female mold 128, a gap 131 corresponding to a shape of the syringe barrel 92 to be molded is formed between the female mold 128 and the male mold 130.

The female mold 128 includes: a first mold 132 formed with molding sections 132a, 132b to mold respective outer surface shapes of the barrel portion 100 and the flange 104 of the syringe barrel 92; and second to fourth molds 136, 138, 140 respectively formed with molding sections 137, 139, 141 to mold an outer surface shape of the cylinder tip portion 102. In the female mold 128, the cavity 129 is formed of the molding sections 132a, 132b, 137, 139, 141.

The first mold 132 is provided with an injection passage 133 in order to inject a molten resin into the gap 131. The injection passage 133 is in communication with the gap 131.

In the syringe barrel 92 according to the present embodiment, the enlarged diameter portion 102b is provided at the cylinder tip portion 102. Therefore, a mold cannot be separated by relatively moving the cylinder tip portion 102 and a mold to mold the outer surface shape of the cylinder tip portion 102 in the axial direction at the time of mold separation in injection molding. Therefore, the mold to mold the cylinder tip portion 102 is divided into the second to fourth molds 136, 138, 140 in order to enable mold separation.

The molding section 137 of the second mold 136 is a unit to mold a half of the outer surface shape (circumferentially half) of the needle holding portion 102a in the cylinder tip portion 102, and is a groove portion having a cross-section formed in a substantially circular arc. The molding section 139 of the third mold 138 is a unit to mold the other half of the outer surface shape (circumferentially half) of the needle holding portion 102a in the cylinder tip portion 102, and is a groove portion having a cross-section formed in a substantially circular arc. The molding section 141 of the fourth mold 140 is a unit to mold the enlarged diameter portion 102b in the cylinder tip portion 102. An entire length and entire circumference of the outer surface shape of the cylinder tip portion 102 are molded by the second to fourth molds 136, 138, 140. Further, the fourth mold 140 is provided with a needle insertion hole 140a into which the needle 93 held at a holding hole 142c of the later-described core 142 is inserted.

The male mold 130 includes: the core 142 to mold the inner surface (inner peripheral portion) of the barrel portion 100 and the proximal-end opening 120; and a holding mold 134 provided with an insertion through-hole 134a through which the core 142 is inserted. More specifically, the core 142 includes: a barrel portion molding section 142a to form the inner surface of the barrel portion 100; and an opening molding section 142b to mold the proximal-end opening 120. Further, the core 142 includes the holding hole 142c to hold a proximal end portion of the needle 93. Further, the holding mold 134 includes a molding section 135 to mold a proximal end surface of the flange 104.

The barrel portion molding section 142a includes a tapered molding section 67, a distal-end side straight molding section 70, and a proximal-end side straight molding section 72 same as a barrel portion molding section 66 of a core 65 illustrated in FIG. 4.

Further, a distal-end side tapered molding section 150 having an outer diameter reduced in the distal end direction is provided on the distal end side of the distal-end side straight molding section 70, with a curved molding section 152 (R molding section) interposed between the distal-end side tapered molding section 150 and the distal-end side straight molding section 70. The curved molding section 152 is a unit to mold the curved portion 118 in the syringe barrel 92 (refer to FIG. 6A). The distal-end side tapered molding section 150 is a unit to mold the distal-end side tapered portion 116 in the syringe barrel 92.

Further, the opening molding section 142b is provided on the proximal end side of the proximal-end side straight molding section 72 as a proximal-end side tapered molding section having an outer diameter reduced in the distal end direction, with a curved molding section 156 (R molding section) interposed between the opening molding section 142b and the proximal-end side straight molding section 72. The curved molding section 156 is a unit to mold the curved portion 122 in the syringe barrel 92.

The syringe barrel 92 and the mold for injection molding 126 according to the present embodiment basically have the above-described structure, and functions and effects thereof will be described below.

Figure 7:
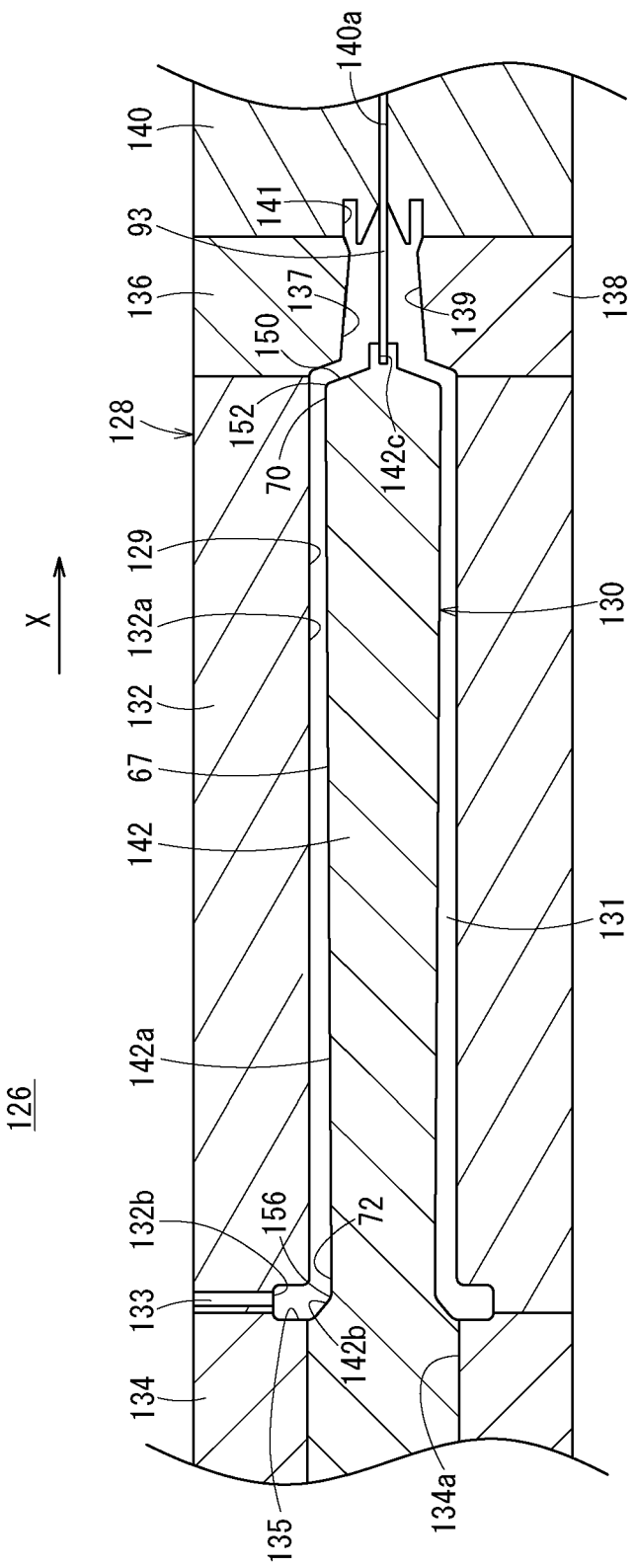
FIG. 7 is a longitudinal sectional view illustrating a mold for injection molding in order to mold the syringe barrel illustrated in FIG. 5.

First, the mold for injection molding 126 is set in a state illustrated in FIG. 7 to mold the syringe barrel 92 by using the above-described mold for injection molding 126. More specifically, the core 142 of the male mold 130 is inserted into the female mold 128 in a state that the proximal end portion of the needle 93 is held at the holding hole 142c of the core 142, and the gap 131 having a shape corresponding to the syringe barrel 92 is formed between the female mold 128 and the male mold 130. Next, the molten resin is injected into the gap 131 via the injection passage 133. Then, after the resin is solidified, the molded syringe barrel 92 is removed from the mold for injection molding 126 (removal process).

In the removal process, the fourth mold 140 is first separated from the cylinder tip portion 102 by moving the fourth mold 140 in the axial direction relative to other molds. More specifically, the fourth mold 140 is separated from the cylinder tip portion 102 by moving the fourth mold 140 in an X-direction in FIG. 7. Almost at the same time, the second mold 136 and the third mold 138 are moved in a direction separating from each other (vertical direction in FIG. 7), thereby separating the second mold 136 and the third mold 138 from the cylinder tip portion 102.

Next, the first mold 132 is separated from the syringe barrel 92 by axially moving the first mold 132 relative to the core 142. More specifically, the first mold 132 is separated from the syringe barrel 92 by moving the first mold 132 in the X-direction while keeping the position of the core 142. In this case, the tapered molding section 67 having the outer diameter that gradually increases toward the distal end is provided at the core 142, and the tapered portion 28 having the inner diameter that gradually increases toward the distal end is formed at the inner peripheral portion 108 of the barrel portion 100 of the syringe barrel 92. Therefore, fitting force between the core 142 and the barrel portion 100 is stronger than fitting force between the first mold 132 and the barrel portion 100. Therefore, along with movement of the first mold 132 in the X-direction, the syringe barrel 92 is surely separated (removed) from the first mold 132 while being held at the core 142.

Next, the syringe barrel 92 is separated from the core 142 by axially moving the holding mold 134 relative to the core 142. More specifically, when the holding mold 134 is moved in the X-direction while holding the position of the core 142, the syringe barrel 92 is pushed in the distal end direction and moved relative to the core 142. This separates the syringe barrel 92 from the core 142. Meanwhile, the barrel portion 100 of the syringe barrel 92 may be grabbed by a chuck or the like and pulled out from the core 142 without moving the holding mold 134 relative to the core 142.

In this case, the gradients of the tapered portion 28 formed in the syringe barrel 92 and the tapered molding section 67 formed at the core 142 are slight. Therefore, there is no problem in moving the syringe barrel 92 relative to the core 142 in the distal end direction. More specifically, along with movement of the syringe barrel 92 relative to the core 142 in the distal end direction, the diameter of the barrel portion 100 is increased (deformed) within an elastic limit. Therefore, the syringe barrel 92 can be separated from the core 142 without damage.

In the above-described manner, the syringe barrel 92 is removed from the mold for injection molding 126.

According to the syringe barrel 92 and the mold for injection molding 126 of the present embodiment, the functions and effects same as the syringe barrel 12 and a mold for injection molding 50 according to the first embodiment can be obtained.

Meanwhile, according to the second embodiment, the needle 93 is held at the needle holding hole 102c by performing insert molding for the needle 93 at the time of molding the syringe barrel 92. However, the proximal end side of the needle 93 may be inserted into the needle holding hole 102c after molding the syringe barrel 92, and the needle 93 may be held at the needle holding hole 102c by heat welding with high-frequency waves or laser, bonding with an adhesive, or the like. In this case, the holding hole 142c is not provided, but the core 142 of the male mold 130 is formed with a needle holding hole forming unit to mold the needle holding hole 102c of the cylinder tip portion 102 at the distal end thereof.

Third Embodiment

Figure 8:
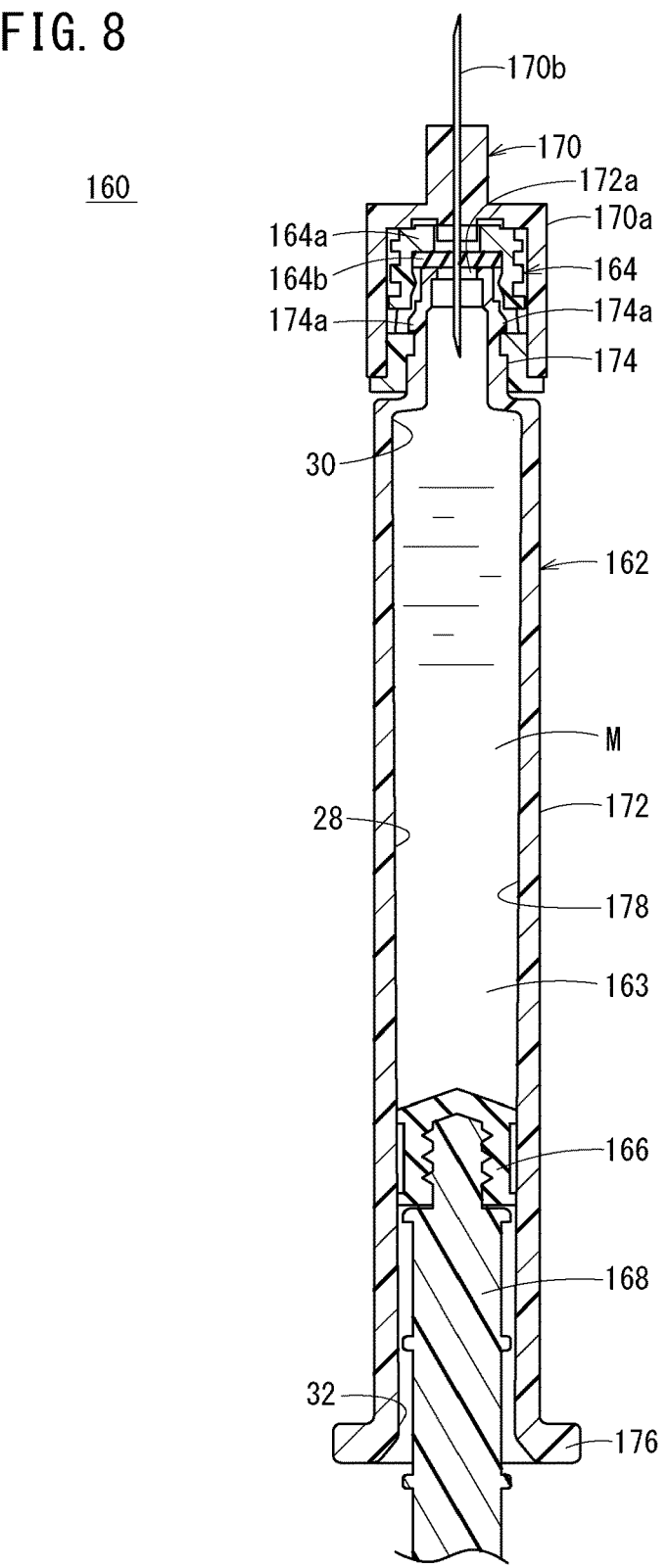
FIG. 8 is a longitudinal sectional view illustrating a syringe including a syringe barrel according to a third embodiment of the present invention.

FIG. 8 is a longitudinal sectional view illustrating a syringe 160 including a syringe barrel 162 according to a third embodiment of the present invention. In the following, portions different from a first embodiment in the syringe barrel 162 will be mainly described.

The syringe 160 includes, as main components, the syringe barrel 162, a cap 164 to seal a distal end opening 172a of the syringe barrel 162, a gasket 166 capable of liquid-tightly sliding inside the syringe barrel 162, a pusher 168 having a distal end connected to the gasket 166, and a drug M filled in a filling chamber 163 formed inside the syringe barrel 162. Thus, the syringe 160 is formed as a prefilled syringe preliminarily filled with the drug M.

The syringe barrel 162 includes a hollow barrel portion 172 constituting a main portion thereof, a cylinder tip portion 174 provided at a distal end of the barrel portion 172, and a flange 176 formed in a manner projecting radially outward from a proximal end of the barrel portion 172.

The barrel portion 172 is a hollow cylindrical shaped portion into which the gasket 166 is inserted in a manner slidable at an inner peripheral portion thereof. Same as an inner peripheral portion 26 of a barrel portion 18 according to the first embodiment, an inner peripheral portion 178 of the barrel portion 172 includes a tapered portion 28, a distal-end side straight portion 30, and a proximal-end side straight portion 32.

Figure 9A:
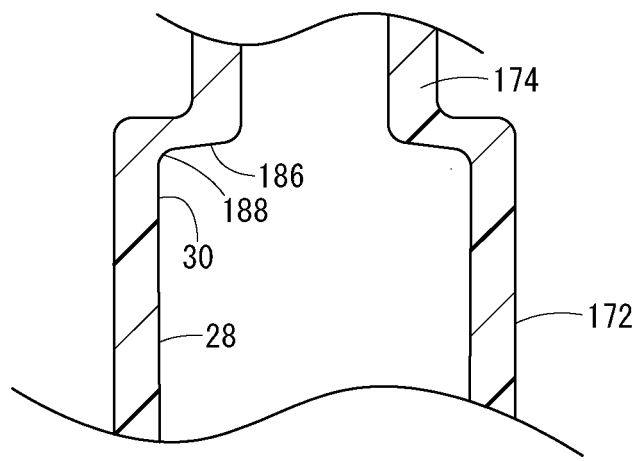
FIG. 9A is an enlarged view illustrating a distal end side of the syringe barrel illustrated in FIG. 8.

As illustrated in FIG. 9A, on a distal end side of the distal-end side straight portion 30, a distal-end side tapered portion 186 having an inner diameter gradually reduced in the distal end direction is provided, with a curved portion 188 (portion R) interposed between the distal-end side straight portion 30 and the distal-end side tapered portion 186. Since the distal-end side straight portion 30 is thus interposed between the tapered portion 28 and the curved portion 188, dimensional accuracy is easily achieved by injection molding for the diameter at the distal end of the tapered portion 28.

Figure 9B:
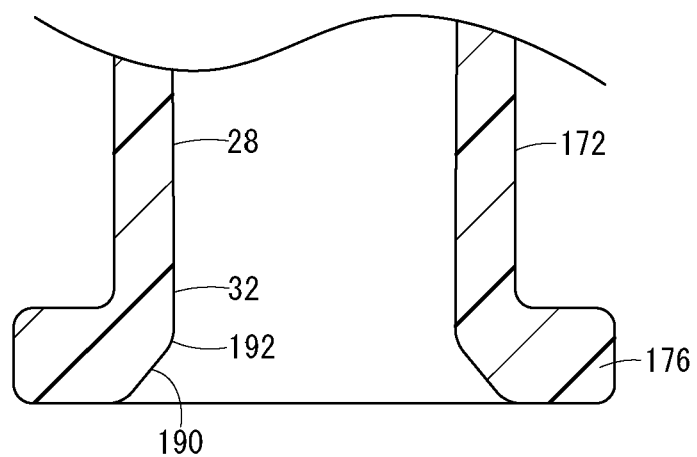
FIG. 9B is an enlarged view illustrating a proximal end side of the syringe barrel illustrated in FIG. 8.

As illustrated in FIG. 9B, on the proximal end side of the proximal-end side straight portion 32, a proximal-end opening 190 is provided as a proximal-end side tapered portion having an inner diameter reduced in the distal end direction, with a curved portion 192 (portion R) interposed between the proximal-end side straight portion 32 and the proximal-end opening 190. Since the proximal-end side straight portion 184 is thus interposed between the tapered portion 28 and the curved portion 192, dimensional accuracy is easily achieved by injection molding for the diameter at the proximal end of the tapered portion 28.

In FIG. 8, the cylinder tip portion 174 having a reduced diameter relative to the barrel portion 172 projects in the distal end direction from a distal end portion of the barrel portion 172.

Volume of the syringe barrel 162 is not limited to specific volume, and the volume can be set in a range of, for example, 0.5 to 100 mL. Further, in this case, the volume of syringe barrel 162 may be set to respective volume of, for example, 0.5 mL, 1 mL, 5 mL, 10 mL, 20 mL, 30 mL, 50 mL, and 100 mL.

Materials constituting the syringe barrel 162 may be those exemplified as materials constituting the syringe barrel 12 according to the first embodiment.

In FIG. 8, the cap 164 includes: a sealing member 164b formed of an elastic material that seals the distal end opening 172a of the cylinder tip portion 174; and a cylindrical main body 164a that supports the sealing member 164b. The main body 164a is fixed to the cylinder tip portion 174 by engagement with an engagement projection 174a provided at the cylinder tip portion 174. In a pre-use state of the syringe 160, the distal end opening 172a of the cylinder tip portion 174 is liquid-tightly sealed by the cap 164 and the drug M is prevented from leaking out from the distal end opening 172a.

The gasket 166 has a structure same as a gasket 16 of the syringe 10 illustrated in FIG. 1. In FIG. 8, the pusher 168 is connected to the gasket 166, but the pusher 168 may also be separated from the gasket 166 before use, and the pusher 168 may be connected to the gasket 166 at the time of use.

When the syringe 160 is used, a needle unit 170 is attached to the cap 164. The needle unit 170 includes: a hollow double-ended needle 170b that can puncture the sealing member 164b; and a cylindrical holder 170a adapted to hold the double-ended needle 170b and detachably attached to the cap 164.

Before using the syringe 160, the needle unit 170 is not attached to the cap 164, and the distal end opening 172a is liquid-tightly closed by the sealing member 164b. The double-ended needle 170b punctures the sealing member 164b when the needle unit 170 is attached to the cap 164 in order to use the syringe 160, and the drug M can be discharged from the distal end opening 172a of the double-ended needle 170b.

Next, a mold for injection molding 196 in order to mold the above-described syringe barrel 162 by injection molding will be described with reference to FIG. 10.

The mold for injection molding 196 includes: a female mold 198 (outer mold) having a cavity 199 that is a recessed portion to mold an outer surface of the syringe barrel 162; and a male mold 200 to form an inner surface of the syringe barrel 162. In a state that a later-described core 212 of the male mold 200 is disposed inside the female mold 198, a gap 201 corresponding to a shape of the syringe barrel 162 to be molded is formed between the female mold 198 and the male mold 200.

The female mold 198 includes: a first mold 202 formed with molding sections 202a, 202b to mold respective outer surface shapes of the barrel portion 172 and the flange 176 of the syringe barrel 162; and second and third molds 206, 208 respectively formed with molding sections 207, 209 to mold an outer surface shape of the cylinder tip portion 174. In the female mold 198, the cavity 199 is formed of the molding sections 202a, 202b, 207, 209.

The first mold 202 is provided with an injection passage 203 in order to inject a molten resin into the gap 201. The injection passage 203 is in communication with the gap 201.

In the syringe barrel 162 according to the present embodiment, the engagement projection 174a is provided at the cylinder tip portion 174. Therefore, mold separation cannot be achieved by relatively moving the cylinder tip portion 174 and a mold to mold the outer surface shape of the cylinder tip portion 174 in an axial direction at the time of mold separation in injection molding. Therefore, the mold to mold the outer surface shape of the cylinder tip portion 174 is divided into the second mold 206 and the third mold 208 in order to enable mold separation.

The molding section 207 of the second mold 206 is a unit to mold a half of the outer surface shape (circumferentially half) of the cylinder tip portion 174 and is a groove portion having a cross-section formed in a substantially circular arc.

The molding section 209 of the third mold 208 is a unit to mold the other half of the outer surface shape (circumferentially half) of the needle holding portion of the cylinder tip portion 174, and is a groove portion having a cross-section formed in a substantially circular arc. An entire length and entire circumference of the outer surface shape of the cylinder tip portion 174 are molded by the second mold 206 and the third mold 208.

The male mold 200 includes: the core 212 to mold an inner surface (inner peripheral portion 178) of the barrel portion 172, the proximal-end opening 190, and the inner surface of the cylinder tip portion 174; and a holding mold 204 provided with an insertion through-hole 205a through which the core 212 is inserted. More specifically, the core 212 includes: a barrel portion molding section 212a to form the inner surface of the barrel portion 172; an opening molding section 212b to mold the proximal-end opening 190; and a cylinder tip portion molding section 212c to mold the inner surface of the cylinder tip portion 174. Further, the holding mold 204 includes a molding section 205 to mold a proximal end surface of the flange 76.

The barrel portion molding section 212a includes a tapered molding section 67, a distal-end side straight molding section 70, and a proximal-end side straight molding section 72 same as a barrel portion molding section 66 of a core 65 illustrated in FIG. 4.

Further, a distal-end side tapered molding section 220 having an outer diameter reduced in the distal end direction is provided on the distal end side of the distal-end side straight molding section 70, with a curved molding section 222 (R molding section) interposed between the distal-end side tapered molding section 220 and the distal-end side straight molding section 70. The curved molding section 222 is a unit to mold the curved portion 188 in the syringe barrel 162 (refer to FIG. 9A). The distal-end side tapered molding section 220 is a unit to mold the curved portion 188 in the syringe barrel 162.

Further, the opening molding section 212b is provided on the proximal end side of the proximal-end side straight molding section 72 as a proximal-end side tapered molding section having an outer diameter reduced in the distal end direction, with a curved molding section 224 (R molding section) interposed between the opening molding section 212b and the proximal-end side straight molding section 72. The curved molding section 224 is a unit to mold the curved portion 192 in the syringe barrel 162 (refer to FIG. 9B).

The syringe barrel 162 and the mold for injection molding 196 according to the present embodiment basically have the above-described structure, and functions and effects thereof will be described below.

Figure 10:
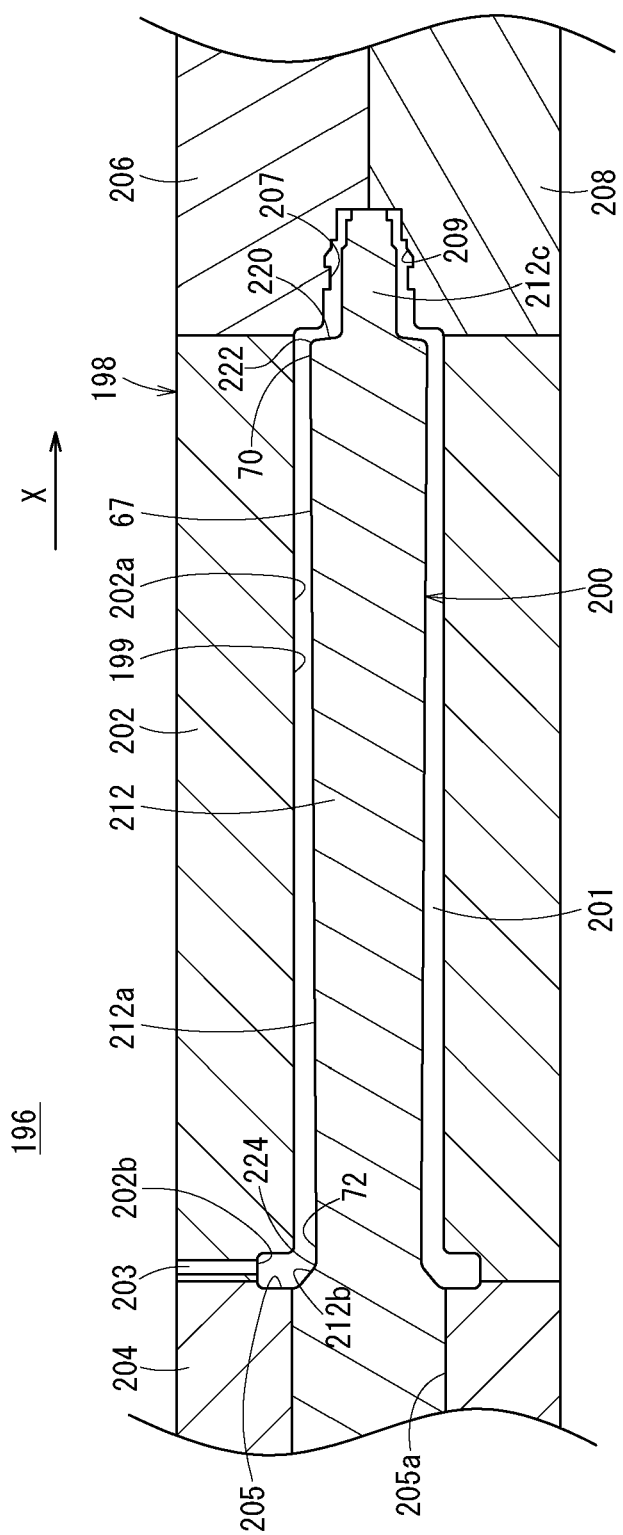
FIG. 10 is a longitudinal sectional view illustrating a mold for injection molding to mold the syringe barrel illustrated in FIG. 8.

First, the mold for injection molding 196 is set in a state illustrated in FIG. 10 in order to mold the syringe barrel 162 by using the above-described mold for injection molding 196. More specifically, the core 212 of the male mold 200 is inserted into the female mold 198, and the gap 201 having a shape corresponding to the syringe barrel 162 is formed between the female mold 198 and the male mold 200. Next, the molten resin is injected into the gap 201 via the injection passage 203 (injection process). Then, after the resin is solidified, the syringe barrel 162 that is the molded syringe barrel is removed from the mold for injection molding 196 (removal process).

In the removal process, the second mold 206 and the third mold 208 are first separated from the cylinder tip portion 174. More specifically, the second mold 206 and the third mold 208 are moved in a direction separating from each other (vertical direction in FIG. 10), thereby separating the second mold 206 and the third mold 208 from the cylinder tip portion 174.

Next, the first mold 202 is separated from the syringe barrel 162 by axially moving the first mold 202 relative to the core 212. More specifically, the first mold 202 is separated from the syringe barrel 162 by moving the first mold 202 in the X-direction while keeping the position of the core 212. In this case, the tapered molding section 67 having the outer diameter that gradually increases toward the distal end is provided at the core 212, and the tapered portion 28 having the inner diameter that gradually increases toward the distal end is formed at the inner surface of the barrel portion 172 of the syringe barrel 162. Therefore, fitting force between the core 212 and the barrel portion 172 is stronger than fitting force between the first mold 202 and the barrel portion 172. Therefore, along with movement of the first mold 202 in the X-direction, the syringe barrel 162 is surely separated (removed) from the first mold 202 while being held at the core 212.

Next, the syringe barrel 162 is separated from the core 212 by axially moving the holding mold 204 relative to the core 212. More specifically, when the holding mold 204 is moved in the X-direction while holding the position of the core 212, the syringe barrel 162 is pushed in the distal end direction and moved relative to the core 212. This separates the syringe barrel 162 from the core 212. Meanwhile, the barrel portion 172 of the syringe barrel 162 may be grabbed by a chuck or the like and pulled out from the core 212 without moving the holding mold 204 relative to the core 212.

In this case, the gradients of the tapered portion 28 formed in the syringe barrel 162 and the tapered molding section 67 formed at the core 212 are slight. Therefore, there is no problem in moving the syringe barrel 162 relative to the core 212 in the distal end direction. More specifically, along with movement of the syringe barrel 162 relative to the core 212 in the distal end direction, the diameter of the barrel portion 172 is increased (deformed) within an elastic limit. Therefore, the syringe barrel 162 can be separated from the core 212 without damage.

In the above-described manner, the syringe barrel 162 is removed from the mold for injection molding 196.

According to the syringe barrel 162 and the mold for injection molding 196 of the present embodiment, the functions and effects same as the syringe barrel 12 and a mold for injection molding 50 according to the first embodiment can be obtained.

Meanwhile, according to the respective embodiments described above, the syringe barrels 12, 92, 162 have structure as the barrel of the prefilled syringe preliminarily filled with the drug M, but the present invention may also be applicable to a syringe barrel not preliminarily filled with the drug M.

While the preferable embodiments of the present invention have been described above, the present invention is not limited to the above embodiments, and needless to mention, various kinds of modifications can be made within a range without departing from the gist of the present invention.

Further, as far as the cylinder tip portion has a shape capable of discharging the drug M filled inside the syringe barrel, the shape is not limited, and the syringe barrel may have a shape including a male lure that can be inserted and connected to a female lure, or a shape including a lock adapter around a male lure. In this case, a portion to mold the barrel portion of the syringe barrel of the mold for injection molding may be same as the above-described respective embodiments, and only a portion to form the cylinder tip portion may be suitably designed.

The invention claimed is:

1. A syringe barrel comprising:
a hollow barrel portion that has a proximal-end opening at a proximal end of the hollow barrel portion and is configured such that a gasket is insertable from the proximal-end opening into the hollow barrel portion; and
a hollow cylindrical tip portion projecting from a distal end of the hollow barrel portion, wherein an outer diameter of the hollow cylindrical tip portion is smaller than an outer diameter of the hollow barrel portion;
wherein the hollow barrel portion extends from a proximal end of the proximal-end opening, which is at a proximal end of the syringe barrel, to a proximal end of the hollow cylindrical tip portion;
wherein an inner peripheral portion of the hollow barrel portion includes a tapered portion in a main area of the inner peripheral portion in an axial direction, the tapered portion having an inner diameter that gradually increases toward a distal end of the tapered portion from a proximal end of the tapered portion; and
wherein the tapered portion extends along 50% or more of an axial length of the hollow barrel portion.

2. The syringe barrel according to claim 1, wherein the tapered portion extends along an entirety of an axial length of the inner peripheral portion of the hollow barrel portion.

3. The syringe barrel according to claim 1, wherein a difference between an inner diameter at the proximal end of the tapered portion and an inner diameter at the distal end of the tapered portion is in a range of 0.01 to 0.07 mm.

4. The syringe barrel according to claim 1, wherein an axial length of the hollow barrel portion is 50 to 60 mm, and a difference between an inner diameter at the proximal end of the tapered portion and an inner diameter at the distal end of the tapered portion is in a range of 0.02 to 0.05 mm.

5. The syringe barrel according to claim 1, wherein a curved portion is provided on a distal end side of the tapered portion at the inner peripheral portion of the hollow barrel portion, with a distal-end side straight portion having a constant inner diameter interposed between the curved portion and the tapered portion.

6. The syringe barrel according to claim 1, wherein a curved portion is provided on a proximal end side of the tapered portion at the inner peripheral portion of the hollow barrel portion, with a proximal-end side straight portion having a constant inner diameter interposed between the curved portion and the tapered portion.

7. The syringe barrel according to claim 1, wherein the syringe barrel is formed of a cyclic olefin polymer or a cyclic olefin copolymer.

8. A mold for injection molding a syringe barrel comprising a hollow barrel portion that has a proximal-end opening at a proximal end and is configured such that a gasket is insertable from the proximal-end opening into the hollow barrel portion, and a hollow cylindrical tip portion projecting from a distal end of the hollow barrel portion, wherein an outer diameter of the hollow cylindrical tip portion is smaller than an outer diameter of the hollow barrel portion, the mold comprising:
a female mold including a recessed portion to mold an outer surface of the syringe barrel, the female mold comprising:
a first mold portion configured to mold an outer surface of the hollow barrel portion, and
a second mold portion configured to mold an outer surface of the hollow cylindrical tip portion,
wherein an inner diameter of the second mold portion is smaller than an inner diameter of the first mold portion; and
a male mold including a core having a hollow barrel portion molding section configured to mold an inner peripheral surface of the hollow barrel portion;
wherein the hollow barrel portion molding section of the core includes an opening molding section configured to mold the proximal-end opening;
wherein the hollow barrel portion molding section extends from a proximal end of the opening molding section, which is at a proximal end of the recessed portion of the female mold, to a proximal end of the second mold portion;
wherein the hollow barrel portion molding section includes a tapered molding section in a main area of the hollow barrel portion molding section in an axial direction, the tapered molding section having an outer diameter that gradually increases toward a distal end of the tapered molding section from a proximal end of the tapered molding section, and
wherein the tapered molding section extends along 50% or more of an axial length of the hollow barrel portion molding section.

* * * * *